United States Patent
Forberg

(10) Patent No.: US 6,857,617 B2
(45) Date of Patent: Feb. 22, 2005

(54) ROLLER PINCHER FOR SETTING THE REGULATION CROSS-SECTION OF A FLEXIBLE TUBING

(76) Inventor: Hans-Jürgen Forberg, Sebenter Weg 44, 23758 Oldenburg (DE)

(*) Notice: Subject to any disclaimer, the term of this patent is extended or adjusted under 35 U.S.C. 154(b) by 0 days.

(21) Appl. No.: 10/770,025

(22) Filed: Feb. 2, 2004

(65) Prior Publication Data

US 2004/0164258 A1 Aug. 26, 2004

(30) Foreign Application Priority Data

Feb. 26, 2003 (DE) .......................... 103 08 118

(51) Int. Cl.$^7$ .......................................... A61M 39/28
(52) U.S. Cl. ................................................ 251/6; 251/4
(58) Field of Search ........................................ 251/4–8

(56) References Cited

U.S. PATENT DOCUMENTS

| | | | |
|---|---|---|---|
| 2,448,741 A | 9/1948 | Scott et al. | |
| 3,802,463 A | 4/1974 | Dabney | |
| 3,893,468 A | 7/1975 | McPhee | |
| 3,918,675 A | 11/1975 | Forberg | |
| 4,406,440 A | * 9/1983 | Kulle et al. | ........... 251/6 |
| 4,475,708 A | 10/1984 | Becker, Jr. | |
| 4,475,709 A | 10/1984 | Becker, Jr. | |
| 4,725,037 A | 2/1988 | Adelberg | |
| 4,856,755 A | 8/1989 | Clarke | |
| 4,869,721 A | 9/1989 | Karpisek | |
| 4,895,340 A | 1/1990 | Forberg | |
| 5,190,079 A | 3/1993 | Nakada | |
| 6,129,330 A | 10/2000 | Guala | |

FOREIGN PATENT DOCUMENTS

| | | |
|---|---|---|
| DE | 22 42 539 | 4/1974 |
| DE | 37 38 965 | 5/1989 |

* cited by examiner

Primary Examiner—Paul J. Hirsch
(74) Attorney, Agent, or Firm—McGlew and Tuttle, P.C.

(57) ABSTRACT

An elongate pinch housing is provided which is U-shaped in cross-section with two sidewalls and with a web wall connecting these. A pinch roller is longitudinally displaceable in these sidewalls with an annular notch at its one circumferential corner region for forming the regulation cross-section of the flexible tubing. The pinch housing in its transition region from the web wall to that sidewall which is distant from the annular notch of the pinch roller is provided with an inner, elongate side guide surface for the flexible tubing. The side guide surface projects into the pinch housing and runs inclined to its longitudinal middle plane so that the flexible tubing inserted in the pinch housing is subjected to a transverse movement.

15 Claims, 2 Drawing Sheets

ROLLER PINCHER FOR SETTING THE REGULATION CROSS-SECTION OF A FLEXIBLE TUBING

FIELD OF THE INVENTION

The invention relates to a roller pincher for setting the regulation cross-section of a flexible tubing

BACKGROUND OF THE INVENTION

The invention proceeds from a roller pincher for setting the regulation cross-section of a flexible tubing which is inserted into the roller pincher and which may be connected to a medical fluid container, wherein the roller pincher comprises an elongate pinch housing u-shaped in cross-section with two sidewalls and with a web wall connecting these, as well as a pinch roller which acts on the flexible tubing positioned in the housing and is arranged longitudinally displaceable in these sidewalls, with an annular notch on its one circumferential corner region for forming the regulation cross-section of the flexible tubing in cooperation of the pinch housing.

The flow cross-section of the flexible tubing may be changed with the help of such a roller pincher by displacing the pinch roller in the pinch housing, and one may thus set the through-flow quantity of a fluid medium.

Such a roller pincher is described in DE 37 38 965 C1. This roller pincher consists of an elongate, U-shaped housing and of a pinch roller displaceable therein guided in the longitudinal direction. The pinch roller at its one circumferential corner region has an annular notch for accommodating an angularly bent longitudinal edge region of the flexible tubing pinched unmovable in position between the pinch roller and the web of the housing, wherein the annular notch, with the sidewall of the pinch housing lying opposite it forms the respective regulating region of the pinch housing. The sidewall is provided with a projecting means in the form of a slanted running ledge for co-setting the regulation cross-section of the flexible tubing so that the regulation cross-section of the flexible tubing is increased or reduced by displacing the roller pincher in the pinch housing.

This roller pincher has proven itself in practice, i.e. the respectively set regulation cross-section remains essentially constant. Since however the material of the used flexible tubing may vary in softness, with relatively soft flexible tubing material there exists the danger that with the return displacement of the pinch roller, i.e. if the regulation cross-section of the flexible tubing is to be enlarged or if with the exact setting of the regulation cross-section a return movement of the pinch roller is effected, flexible tubing material in the upper region of the ledge-like setting means is rigidly pinched. The result of this it that in such a case the desired regulation cross-section of the flexible tubing may not be precisely set and/or that the flexible tubing is damaged along the adjustment, or setting, length of its regulation cross-section in the pinch housing.

A further roller pincher is known from DE 22 42 539 C2. On a longitudinal edge of the web of the pinch housing it is provided with a channel-like relief tapering in particular in width, which has such a depth that the section of this flexible tubing forming the regulation cross-section of the flexible tubing given bending at an angle may be freely jammed into the respective cross-section location of the relief. The cross-section of the relief changes continuously in the longitudinal direction so that the corresponding regulation cross-section of the flexible tubing may be set on displacement of the pinch roller. On the other longitudinal edge region of the housing web which faces away from the channel-like relief there is provided a fixing prominence which retains the flexible tubing which is pinched between the pinch roller and the web and which may not be flown through at this location, in a manner in which it fixed on all sides. By way of this design the flexible tubing may not be optimally set for achieving an exact and constant regulation cross-section along the regulation length of the pinch housing.

BRIEF SUMMARY OF THE INVENTION

The object of the invention lies in improving a roller pincher of the initially specified type to the extent that a damage to the flexible tubing along a setting section in the pinch housing is avoided and an optimal setting of the flexible tubing in the pinch housing is ensured for achieving an exact and constant regulation cross-section of the flexible tubing along a setting length.

The solution of the object is specified in a roller pincher for setting the regulation cross-section of a flexible tubing which is connectable to a medical fluid container. The roller pincher comprises an elongate pinch housing being U-shaped in cross-section with two sidewalls and with a web wall connecting these sidewalls. A pinch roller acts on the flexible tubing positioned in the housing and is arranged longitudinally displaceable in these sidewalls. The pinch roller has an annular notch on its one circumferential corner region for forming the regulation cross-section of the flexible tubing in cooperation with the pinch housing. The pinch housing in its transition region from the web wall to that sidewall which is distant to the annular notch of the pinch roller comprises an inner, elongate side guide surface for the flexible tubing held between the web wall and the pinch roller. The side guide surface projecting into the pinch housing and running inclined to its longitudinal middle plane.

The advantages which may be achieved with the solution according to the invention in particular lies in the fact that on adjusting the pinch roller, preferably with the return setting of the pinch roller in the pinch housing, i.e. a setting of the pinch roller in that position in which the regulation cross-section of the flexible tubing located in the roller pincher becomes larger, damage to the flexible tubing along the setting length of the pinch roller is avoided, in particular with very soft flexible tubing material. That flexible tubing length region which faces the notch of the pinch roller and thus the regulation cross-section of the flexible tubing, on setting the pinch roller is gently subjected to the regulation procedure on setting the pinch roller by way of the side guide surface provided on the other side of the pinch housing according to the invention. The side guide surface effects a forward displacement of the flexible tubing transverse to its longitudinal direction under the pinch roller in the direction of the regulation cross-section. Thus also with soft materials an optimal position of the flexible tubing in its respective pinching and regulation position is ensured. By way of the transverse displacement of the flexible tubing furthermore a larger regulation cross-section of the flexible tubing is achieved which is advantageous for nutrient solutions containing roughage.

In one advantageous design of the side guide surface of the pinch housing according to the invention this is provided on a ledge-like projection which is preferably formed of one piece with the sidewall and the web wall of the pinch housing. By way of this design the side guide surface may be created in a simple manner on injection molding the roller pincher.

In a further advantageous design the side guide surface of the pinch housing runs at an obtuse angle to the web wall of the pinch housing. By way of this design the corresponding side region of the flexible tubing is brought into its transverse position in the pinch housing in a gentle manner on displacing the pinch roller.

The side guide surface of the pinch housing according to the invention is particularly advantageous if, as a pincher auxiliary means for setting the regulation cross-section of the flexible tubing, an adjustment groove is provided in that sidewall of the clamping housing which faces the annular notch of the pinch roller. The side guide surface according to the invention effects a damage-free introduction and guiding of the flexible tubing region forming the regulation cross-section into or in the adjustment groove along the entire setting length for the regulation cross-section. Thus here too it is ensured in particular with soft flexible tubing material that the flexible tubing is not damaged along its regulation length during the setting of the regulation cross-section.

In another advantageous design the base surface of the adjusting groove likewise runs inclined to the longitudinal middle plane of the pinch housing. With regard to this, a particular design lies in the fact that the base surface of the adjusting groove runs equidistant to the side guide surface of the pinch housing according to the invention. A particularly simple embodiment for this is if the base surface of the adjusting groove and the side guide surface according to the invention run parallel to one another.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE INVENTION

Figure 1:
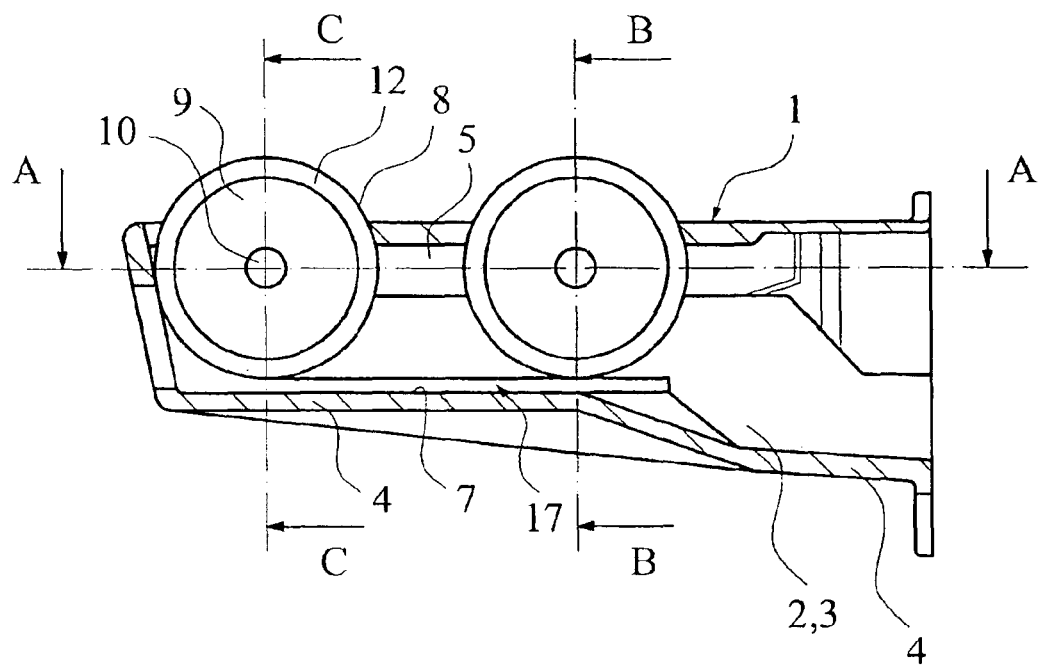
FIG. 1 a first longitudinal section through the embodiment example according to line D—D in FIG. 2.

The roller pincher according to FIG. 1 consists in the usual manner of an elongate, U-shaped plastic pinch housing 1 preferably manufactured in an injection molding method, with two sidewalls 2 and 3 as well as a web wall 4. Guide grooves 5 running parallel to the web wall 4 are machined into the sidewalls 2 and 3, and these grooves in the known manner are open to the one end of the clamping housing 1 open at both ends, in order to be able to arrange the pinch roller in the housing 1. The inner surface 7 of the web wall 4 forms the pinch surface for flexible tubing 6 which is only shown in the FIGS. 3 and 4 and here is pinched in by the circumferential surface 8 of a pinch roller 9. The pinch roller 9 in its center comprises pivot pegs 10 arranged on both sides which engage into the guide grooves 5. The circumferential surface 8 of the pinch roller 9 is designed such to have a good grip, for example by way of knurling, and lies at a distance opposite the pinch surface 7 which due to the play between the peg 10 and the associated groove 5 is slightly smaller than double the wall thickness of the flexible tubing 6. According to the FIGS. 3 and 4 a first pinch region of the flexible tubing 6 is pinched in between the circumferential surface 8 of the pinch roller 9 and the pinch surface 7 of the housing web wall 4 in a manner such that no flow cross-section is formed in this region of the flexible tubing, but that the flexible tubing is held in the housing 1 in a gentle manner, i.e. without destruction and in transversely movable manner.

Figure 3:
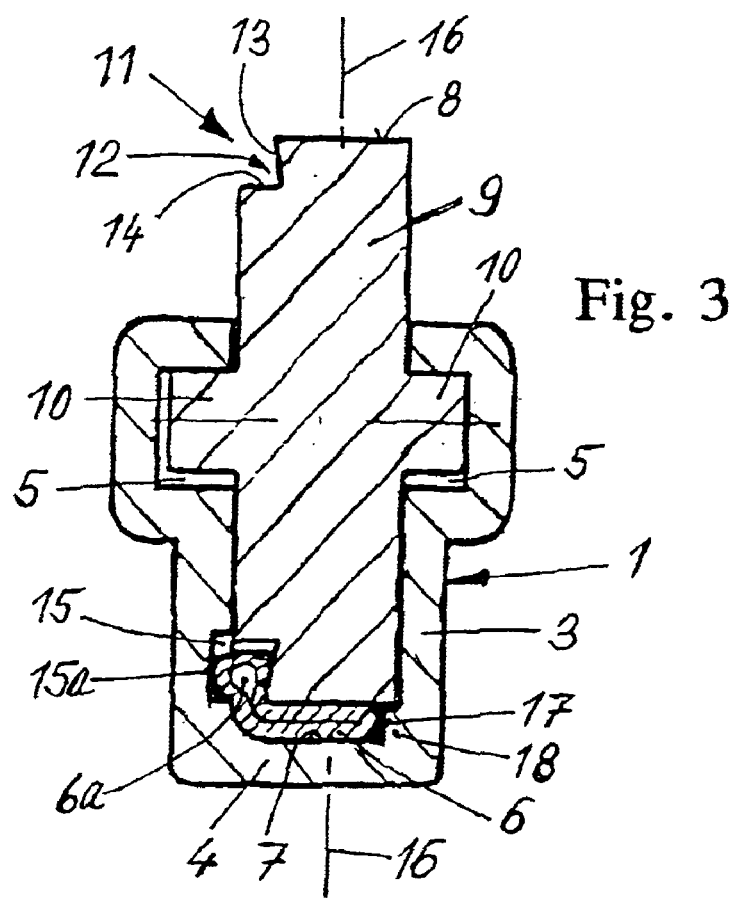
FIG. 3 a cross-section through the roller pincher according to line B—B in FIG. 1.
Figure 4:
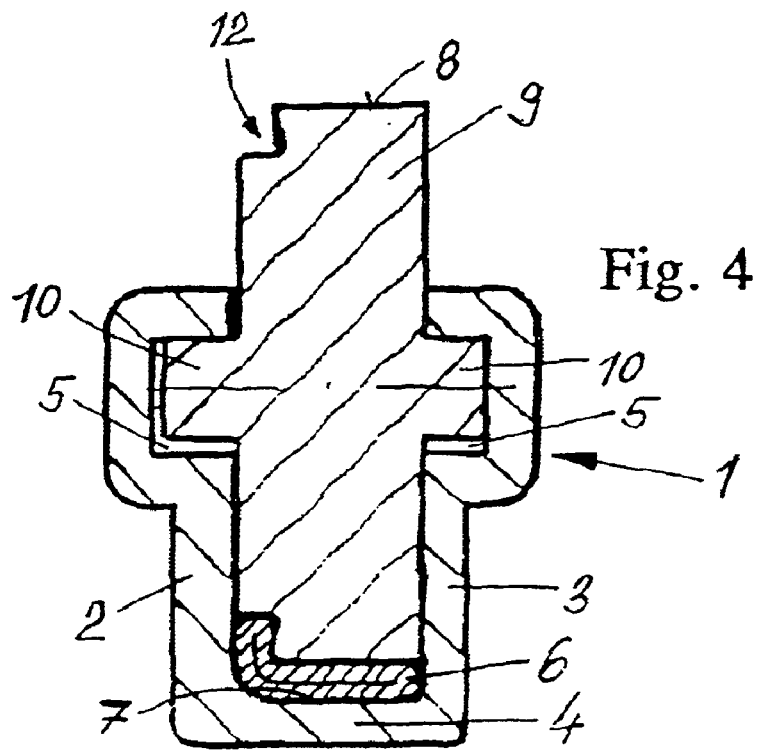
FIG. 4 a further cross-section through the roller pincher according to line C—C in FIG. 1.

As one may best recognize from FIGS. 3 and 4, the pinch roller 9 on its one circumferential corner region 11 comprises a concentric annular notch 12 with a radial contact surface 13 and with a contact surface 14 parallel to the rotational axis of the pinch roller. The radial contact surface 12 is preferably designed such that it springs back so that it runs inclined with respect to the pinch surface 7 of the web wall 4. The course of the inclination is to be recognized in the FIGS. 3 and 4.

The contact surfaces 13 and 14 form a first wall limitation for forming a local regulation cross-section 6a as a remaining transverse region of the flexible tubing 6. One recognizes that the region of the flexible tubing which in each case forms this regulation cross-section, according to FIGS. 3 and 4, engages bent at an angle into the annular notch 11 of the clamping roller 9.

As a second and last wall limitation for forming the respective regulation cross-section 6a of the flexible tubing 6 there is provided the sidewall 2 of the clamping housing 1 which lies opposite the contact surface 13 of the annular notch 12 of the roller pincher 9. This sidewall 2 according to FIG. 3 is preferably provided with an adjusting groove 15 whose base surface 15a is designed in a cross-section-reducing manner so that this sets the respectively required regulation cross-section 6a of the flexible tubing 6 on displacing the pinch roller 9. In order to achieve the cross-sectional change of the regulation cross-section the base surface 15a of the adjusting groove 15 runs inclined to the longitudinal middle plane 16 of the clamping housing 1 as this is clearly seen in FIG. 2. The inclined course of the base surface 15a may itself be plane or be designed curved in a slightly convex or concave manner which depends on the respective application case. The groove 15 or its base surface 15a thus forms the adjusting means which on displacing the pinch roller 9 co-effects a change in the size of the regulation cross-section 6a.

As FIG. 3 shows, the adjusting groove 15 is formed rectangular in cross-section in a manner such that its base surface 15a runs at a right angle to the inner surface 7 of the web wall 4. One may alternatively proceed in that the base surface 15a encloses an obtuse angle (not shown) with the mentioned inner surface 7. By way of this one avoids a too great a kinking of the outer wall of the flexible tubing in the transition region between the regulation cross-section 6a and the remaining pinch cross-section of the flexible tubing 6 so that a gentle deformation of the flexible tubing is given in this transition region.

Figure 2:
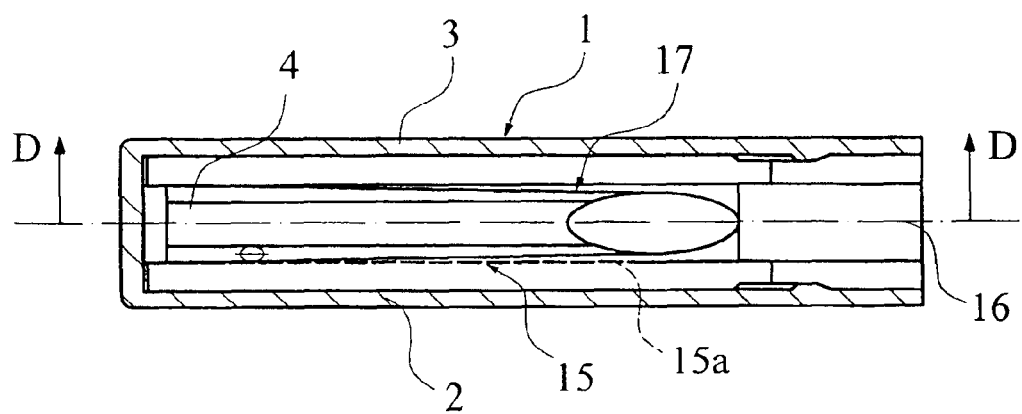
FIG. 2 a second longitudinal section through the roller pincher according to line A—A in FIG. 1.

As may best be seen in the FIGS. 2 and 3 the clamping housing 1 in its transition region from the other sidewall 3 which is distant to the annular notch 12 of the pinch roller 9, to the web wall 4 of the pinch housing is provided with an inner, elongate side guide surface 17 for the flexible tubing 6 held between the web wall 7 and the circumferential surface 8 of the pinch roller 9. As FIG. 2 in particular shows, the side guide surface 17 runs gradually into the inside of the housing in a projecting manner, and specifically in a manner such that it is inclined towards the longitudinal middle plane 16 of the housing 1. The projecting course of the side guide surface is directed in the direction of the sidewall 2 so that the slightly pinched region of the tubing 6 is moved guided transversely to the longitudinal region of the pinch housing as is to be recognized in FIG. 2 and with a comparison to FIGS. 3 and 4.

The side guide surface 17 of the pinch housing 1 is preferably provided on a ledge-like projection 18. This projection 18 is formed as one piece or integral with the sidewall 3 and the web wall 4 of the pinch housing 1 so that this projection may be coformed in a simple manner with the injection-molding manufacture of the housing 1.

The side guide surface 17 may, as shown in FIG. 3, form a right angle with the web wall 4 of the clamping housing 1. It is however also possible for the side guide wall to enclose an obtuse angle with this web wall, which improves the side guiding of the flexible tubing 6. With reference to FIG. 2 it is to be recognized that the inclined running side guide surface 17 itself is formed plane. According to FIG. 2 the base surface 15a of the adjusting groove 15 is likewise formed plane. Both surfaces 15a and 17 run further such that an equidistant distance exists along their length between the two.

In the shown case according to FIG. 2 the base surface 15a and the side guide surface 17 run parallel or essentially parallel to one another. An equidistant course of these two surfaces to one another is also given if these two surfaces run curved in the same direction. Such a curved run of the two surfaces will be naturally very weak. If for example the side guide surface 17 runs curved in a weakly convex manner, the base surface 15a runs curved too in a weakly concave manner. As a further alternative it is also possible for the one surface 15a or 17 to run straight or plane, and the respective other surface to run in a weakly curved manner. In this case no equidistant course is given.

FIG. 1 is to be understood such that usually only a single pinch roller 9 is provided. The position B—B in FIG. 1 means that this pinch roller 9 is located in its one end position in which the regulation cross-section 6a of the flexible tubing applied into the pinch roller is at its greatest, as this is shown in FIG. 3. In the other end position of the pinch roller 9 which is represented in FIG. 1 by the position C—C, the flexible tubing 6 is completely closed, i.e. it no longer has any actual regulation cross-section, which corresponds to the representation of the flexible tubing in FIG. 4. Between the two previously mentioned end positions of the pinch roller 9 the respective desired intermediate regulation cross-sections of the flexible tubing 6 are set by displacing the pinch roller 9 with a rotation into the guide grooves 5 in the usual manner.

While specific embodiments of the invention have been shown and described in detail to illustrate the application of the principles of the invention, it will be understood that the invention may be embodied otherwise without departing from such principles.

What is claimed is:

1. A roller pincher for setting a regulation cross-section of a flexible tubing which is connectable to a medical fluid container, the roller pincher comprising:

an elongate pinch housing being U-shaped in cross-section with two sidewalls and with a web wall connecting said side walls;

a pinch roller which acts on the flexible tubing positioned in said housing, said pinch roller being arranged longitudinally displaceable in said sidewalls, said pinch roller having an annular notch on one circumferential corner region for forming the regulation cross-section of the flexible tubing in cooperation with said pinch housing, wherein said pinch housing in a transition region from said web wall to one of said sidewalls which is distant to said annular notch of the pinch roller, said transition region comprises an inner elongate side guide surface for the flexible tubing held between the web wall and the pinch roller, said side guide surface projecting into said pinch housing and running inclined to a longitudinal middle plane of said housing.

2. A roller pincher according to claim 1, wherein said side guide surface of said pinch housing is provided on a ledge-like projection.

3. A roller pincher according to claim 2, wherein said projection is formed in one piece with said one sidewall and said web wall of said pinch housing.

4. A roller pincher according to claim 1, wherein said side guide surface of said pinch housing runs at an obtuse angle to said web wall of said pinch housing.

5. A roller pincher according to claim 2, wherein said side guide surface of said pinch housing runs at an obtuse angle to said web wall of said pinch housing.

6. A roller pincher according to claim 3, wherein said side guide surface of said pinch housing runs at an obtuse angle to said web wall of said pinch housing.

7. A roller pincher according to claim 1, wherein an adjusting groove is allocated to said side guide surface of said pinch housing in the other said sidewall of said housing which faces said annular notch of said pinch roller, whose cross-section changes along a displacement path of said pinch roller for setting the respective regulation cross-section of the flexible tubing.

8. A roller pincher according to claim 6, wherein an adjusting groove is allocated to said side guide surface of said pinch housing in the other said sidewall of said housing which faces said annular notch of said pinch roller, whose cross-section changes along a displacement path of said pinch roller for setting the respective regulation cross-section of the flexible tubing.

9. A roller pincher according to claim 7, wherein a base surface of said adjusting groove runs inclined to said longitudinal middle plane of said pinch housing.

10. A roller pincher according to claim 8, wherein a base surface of said adjusting groove runs inclined to said longitudinal middle plane of said pinch housing.

11. A roller pincher according to claim 7, wherein a base surface of said adjusting groove runs equidistant to said side guide surface of said pinch housing.

12. A roller pincher according to claim 10, wherein said base surface of said adjusting groove runs equidistant to said side guide surface of said pinch housing.

13. A roller pincher according to claim 7, wherein a base surface of said adjusting groove runs parallel or essentially parallel to said side guide surface of said pinch housing.

14. A roller pincher according to claim 10, wherein a base surface of said adjusting groove runs parallel or essentially parallel to said side guide surface of said pinch housing.

15. A roller pincher arrangement for a flexible tube, the arrangement comprising:

a pinch roller having a circumferential corner region defining an annular notch;

an elongate pinch housing having a U-shaped cross-section with first and second sidewalls and with a base wall connecting said side walls, said pinch roller being arranged in said pinch housing with said annular notch being arranged adjacent said first sidewall and forming a regulation cross-section of the flexible tube in cooperation with said pinch housing, said pinch housing having a transition region from said base wall to said second sidewall, said transition region including an inner elongate side guide surface for the flexible tube held between said base wall and said pinch roller, said side guide surface projecting into said pinch housing and running inclined to a longitudinal middle plane of said housing.

\* \* \* \* \*